United States Patent
Zeller

(10) Patent No.: US 11,221,387 B2
(45) Date of Patent: Jan. 11, 2022

(54) AUTOMATIC DETERMINATION OF A CORRECTION FACTOR FOR PRODUCING MAGNETIC RESONANCE IMAGES

(71) Applicant: Siemens Healthcare GmbH, Erlangen (DE)

(72) Inventor: Mario Zeller, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 0 days.

(21) Appl. No.: 16/851,416

(22) Filed: Apr. 17, 2020

(65) Prior Publication Data
US 2020/0333420 A1 Oct. 22, 2020

(30) Foreign Application Priority Data

Apr. 17, 2019 (DE) .......................... 102019205589.3

(51) Int. Cl.
*G01R 33/565* (2006.01)
*G01R 33/56* (2006.01)
(Continued)

(52) U.S. Cl.
CPC ... *G01R 33/56554* (2013.01); *G01R 33/5608* (2013.01); *G01R 33/5616* (2013.01); *G01R 33/58* (2013.01)

(58) Field of Classification Search
CPC .......... G01R 33/56554; G01R 33/5608; G01R 33/5616; G01R 33/58; G01R 33/56572;
(Continued)

(56) References Cited

U.S. PATENT DOCUMENTS 6,700,374 B1 * 3/2004 Wu .................. G01R 33/56554
324/306
2011/0234228 A1 9/2011 Block
(Continued)

FOREIGN PATENT DOCUMENTS

DE 102010012599 A1 9/2011
DE 102011077197 A1 12/2012

OTHER PUBLICATIONS

German Office Action for German Application No. 10 2019 205 589.3 dated Feb. 12, 2020.
(Continued)

*Primary Examiner* — Susan S Lee
(74) *Attorney, Agent, or Firm* — Lempia Summerfield Katz LLC

(57) ABSTRACT

Automatically determining a correction factor for producing MR images includes outputting a first readout gradient along a readout dimension, reading out a first MR signal from a subject during the output of the first readout gradient, and specifying a second readout gradient having a theoretically identical gradient moment to the first readout gradient. A temporal waveform that differs from a temporal waveform of the first readout gradient is specified for the second readout gradient. The second readout gradient is output along the readout dimension. A second MR signal is read out from the subject during the output of the second readout gradient. A first extent of a representation of the subject is determined based on the first MR signal. A second extent of a representation of the subject is determined based on the second MR signal. A correction factor is obtained from a ratio between the first and second extents.

20 Claims, 8 Drawing Sheets

(51) Int. Cl.
*G01R 33/561* (2006.01)
*G01R 33/58* (2006.01)

(58) Field of Classification Search
CPC .. G01R 33/4824; G01R 33/4818; A61B 5/055
See application file for complete search history.

(56) References Cited

U.S. PATENT DOCUMENTS

| | | | |
|---|---|---|---|
| 2012/0313640 A1 | 12/2012 | Pfeuffer | |
| 2013/0285656 A1* | 10/2013 | Feiweier | G01R 33/56572 324/309 |
| 2013/0307538 A1* | 11/2013 | Pfeuffer | G01R 33/583 324/314 |
| 2013/0307539 A1* | 11/2013 | Pfeuffer | G01R 33/4836 324/314 |
| 2019/0178965 A1* | 6/2019 | Paul | G01R 33/58 |

OTHER PUBLICATIONS

Kim, Yoon-Chul, Jon-Fredrik Nielsen, and Krishna S. Nayak. "Automatic correction of echo-planar imaging (EPI) ghosting artifacts in real-time interactive cardiac MRI using sensitivity encoding." Journal of Magnetic Resonance Imaging: An Official Journal of the International Society for Magnetic Resonance in Medicine 27.1 (2008): 239-245.

Porter, David A., and Robin M. Heidemann. "High resolution diffusion-weighted imaging using readout-segmented echo-planar imaging, parallel imaging and a two-dimensional navigator-based reacquisition." Magnetic Resonance in Medicine: An Official Journal of the International Society for Magnetic Resonance in Medicine 62.2 (2009): 468-475.

Van der Zwaag, Wietske, et al. "Minimization of Nyquist ghosting for echo-planar imaging at ultra-high fields based on a "negative readout gradient" strategy." Journal of Magnetic Resonance Imaging: An Official Journal of the International Society for Magnetic Resonance in Medicine 30.5 (2009): 1171-1178.

Zaitsev, M., J. Hennig, and O. Speck. "Point spread function mapping with parallel imaging techniques and high acceleration factors: fast, robust, and flexible method for echo-planar imaging distortion correction." Magnetic Resonance in Medicine: An Official Journal of the International Society for Magnetic Resonance in Medicine 52.5 (2004): 1156-1166.

* cited by examiner

AUTOMATIC DETERMINATION OF A CORRECTION FACTOR FOR PRODUCING MAGNETIC RESONANCE IMAGES

This application claims the benefit of German Patent Application No. 10 2019 205 589.3, filed Apr. 17, 2019, which is hereby incorporated by reference in its entirety.

BACKGROUND

The present embodiments relate to automatically determining a correction factor for producing magnetic resonance images.

In a magnetic resonance (MR) examination, it is common practice to apply a relatively strong main magnetic field (e.g., of 1.5 or 3 or 7 Tesla) to a subject under examination (e.g., to a patient). This may be achieved by positioning the subject under examination inside an acquisition region of a magnetic resonance system. By positioning the subject under examination within the relatively strong main magnetic field, nuclear spins (e.g., water proton spins) usually become aligned in parallel or anti-parallel with the direction of the main magnetic field inside the subject under examination. At the same time, the nuclear spins precess about the direction of the main magnetic field at a Larmor frequency. The Larmor frequency depends on, for example, the type of the nuclei and on the magnetic flux density of the main magnetic field.

Since the parallel alignment of the nuclear spins with the main magnetic field represents a state of thermal and energy equilibrium, it is often the case that a net magnetization becomes aligned in parallel with the main magnetic field. The net magnetization, referred to below also as the magnetization, appears as the effective macroscopic magnetization of the individual magnetic dipole moments of the nuclear spins.

A gradient coil unit may be used to output additional and spatially varying magnetic fields (e.g., magnetic field gradients). A consequently position-dependent Larmor frequency along the spatial dimension of the magnetic field gradients hence makes spatial encoding possible within a region under examination. Radiofrequency (RF) pulses (e.g., excitation pulses or saturation pulses) may be output by a radiofrequency antenna unit. If an RF pulse is resonant with the Larmor frequency of the nuclear spins, this may result in excitation (e.g., deflection) of the nuclear spins out of a state of equilibrium. The resultant transverse component of the precession of the net magnetization about the direction of the main magnetic field may produce induction in the RF antenna unit. At the same time, the transverse component of the net magnetization decreases (e.g., exponentially) with a transverse relaxation time constant. As this happens, an MR signal (e.g., a free induction decay (FID)) may be detected by the RF antenna unit. In addition, a longitudinal relaxation of the net magnetization back to the state of thermal equilibrium takes place.

Magnetic resonance images of the subject under examination may be reconstructed by the detected MR signals, which are spatially encoded, for example, by the output of magnetic field gradients.

If a plurality of MR signals are read out after a single excitation pulse is output, then the variation over time of a relaxation of the nuclear spins may be detected. The time length between outputting the excitation pulse and reading out an MR signal is often referred to as the echo time (TE).

The output of a plurality of gradients (e.g., along different spatial dimensions) and of RF pulses is often grouped in a sequence (e.g., a pulse sequence or MR sequence). The sequences often also include a succession of readout windows (ADC) over time, within which MR signals may be read out.

It is known from the prior art that artifacts often arise, for example, when producing MR images using sequences that perform radial and/or segmented sampling of k-space.

Examples of sequence types using radial and/or spiral k-space sampling are: PETRA (Pointwise Encoding Time Reduction with Radial Acquisition); and PROPELLER (Periodically Rotated Overlapping Parallel Lines with Enhanced Reconstruction).

Examples of sequence types using segmented k-space sampling are: segmented EPI (Echo Planar Imaging) sequence; and RESOLVE (Readout Segmentation of Long Variable Echo Trains).

The cause of the artifacts is often that compliance with a gradient moment of a readout gradient that is specified by the sequence is not exact because the readout gradient has a modified waveform when the readout gradient is output. The gradient moment of a readout gradient is determined, for example, by an amplitude integral of the temporal waveform during the output of the readout gradient. A discrepancy between the specified gradient moment and the gradient moment that is output may result, for example, in a translation of a read-out spoke and/or row in k-space with respect to a center of k-space. It is therefore advantageous to determine a correction factor such that a specified gradient moment is satisfied when a readout gradient is output.

A number of approaches for determining a suitable correction factor are known for this from the prior art. In order to determine the correction factor, it is common practice to produce a plurality of MR images having different correction factor values from a predefined range. Then, by manual or automatic selection of the MR image containing the fewest artifacts, it is possible to determine the associated correction factor. These methods require additional measurement time and are based on analyzing the artifacts in the MR images produced.

SUMMARY AND DESCRIPTION

The scope of the present invention is defined solely by the appended claims and is not affected to any degree by the statements within this summary.

The present embodiments may obviate one or more of the drawbacks or limitations in the related art. For example, faster yet also reliable determination of a correction factor for producing magnetic resonance images is provided.

A first readout gradient is output along a readout dimension. The first readout gradient may be specified, for example, to have an initial polarity that is opposite to the polarity of a gradient output earlier in time for prephasing a magnetization. In addition, a first MR signal from the subject under examination is read out during the output of the first readout gradient. Thereafter, a second readout gradient having a theoretically identical gradient moment to the first readout gradient is specified. In this case, a temporal waveform that differs from a temporal waveform of the first readout gradient is specified for the second readout gradient.

The first readout gradient may thus have a first temporal waveform, and the second readout gradient may have a second temporal waveform that differs from the first temporal waveform. The second readout gradient may be specified to have an initial polarity that is opposite to the final polarity of the readout gradient output immediately before along the readout dimension.

In addition, the second readout gradient is output along the readout dimension (e.g., along the same readout dimension along which the first readout gradient is also output). A second MR signal from the subject under examination is read out during the output of the second readout gradient. In addition, a first extent of a representation of the subject under examination is determined based on the first MR signal, and a second extent of a representation of the subject under examination is determined based on the second MR signal. A correction factor is obtained from, for example, a ratio between the first extent and the second extent.

The theoretically identical gradient moment of the second readout gradient may be, for example, a gradient moment that is meant to be exactly the same size as the gradient moment of the first readout gradient. The theoretically identical gradient moment may also refer to, for example, a gradient moment that is supposed to be identical and/or intended to be identical and/or planned to be identical.

For example, an excitation pulse may be output before reading out the at least one first MR signal and/or the at least one second MR signal. The excitation pulse is formed by an RF pulse. The excitation pulse may cause the magnetization to be deflected out of a state of equilibrium. The excitation pulse may be configured to deflect (e.g., selectively) only one predefined resonance frequency range of the magnetization of the subject under examination.

In order to specify the second readout gradient, it is possible, for example, to use a value of a scaling factor to adjust a parameter value. The parameter value specifies a temporal waveform of the second readout gradient. The scaling factor may be information about a congruence transformation between the theoretical gradient moments of the temporal waveforms of the first readout gradient and the second readout gradient. By adjusting the parameter value, the second readout gradient may then be specified to have a theoretically identical gradient moment to the first readout gradient.

The parameter value may, for example, include information about a gradient moment, a temporal waveform of a gradient, an output duration of a gradient, and/or a polarity of a gradient. A sequence may be formed from a combination of a plurality of parameter values (e.g., also to predefine other elements of a magnetic resonance examination, such as RF pulses).

In addition, the scaling factor for adjusting the parameter value may be configured to allow scaling of the temporal waveform of the second readout gradient. This involves multiplying, for example, every specified point along the temporal waveform of the readout gradient by a value of the scaling factor that is constant over time. This may hence make it possible to adjust the gradient moment of the second readout gradient while retaining the specified temporal waveform. For example, a shape of the temporal waveform is preserved in this process, while the scaling of the temporal waveform allows an amplitude integral to be adjusted. By adjusting the amplitude integral of the temporal waveform of the second readout gradient, the gradient moment may be adjusted and/or corrected directly.

The method makes it possible to thereby correct a difference between the theoretical gradient moment and the outputted gradient moment without knowing the actually outputted temporal waveform of the second readout gradient.

A congruence transformation between the gradient moments of the temporal waveforms of the first readout gradient and the second readout gradient may include, for example, a ratio between the effective amplitude integrals of the temporal waveforms. The effective amplitude integral provides, for example, a normalized measure (e.g., normalized with respect to a rectangular temporal waveform) of the temporal waveform that currently exists. The congruence transformation may determine a scaling factor that, by adjusting the second parameter value, brings the temporal waveforms of the first readout gradient and the second readout gradient into congruence in terms of the amplitude integrals of the two waveforms. The theoretically identical gradient moment to the first readout gradient may thereby be specified ideally for the second readout gradient.

Reading out the first MR signal and second MR signal during the output of respective readout gradients along the readout dimension performs frequency encoding of the respective MR signal. The first MR signal and the second MR signal are hence signals in k-space that are resolved in at least one dimension. In other words, the output of the readout gradient allows frequency encoding of the at least one MR signal along a readout dimension in which the readout gradient is output. A readout dimension may be, for example, a spatial dimension. The readout dimension does not constrain a direction along the readout dimension. Thus, the output along the readout dimension may take place both in a positive direction and in the negative direction opposite thereto along the readout dimension.

The gradient for prephasing the magnetization, which may be output before the first readout gradient, may be output within the same readout dimension as the first readout gradient and the second readout gradient. The readout dimension does not constrain a polarity of the gradient for prephasing.

The formation of at least one gradient echo may be facilitated as a result of the first readout gradient being specified to have an opposite initial polarity with respect to the prephasing gradient. The initial polarity may denote, for example, a polarity of the first readout gradient immediately at the start of the output of the gradient.

In addition, a readout direction along the readout dimension may be reversed by specifying an initial polarity of the second readout gradient that is opposite to the final polarity of the readout gradient that was output immediately before (e.g., of the first readout gradient). This may facilitate, for example, the formation of a further gradient echo, which may be read out, for example, as the second MR signal. The final polarity may denote a polarity of the first readout gradient immediately at the time the output of the gradient ends.

An extent of a representation of the subject under examination based on an MR signal may be considered to be a spatial extent of the representation in image space. By the known transformation of the MR signal from k-space into an image space, which includes an inverse Fourier transform in at least one dimension, producing an MR image may be dispensed with. For example, a reference value for correcting the outputted gradient moment of the second readout gradient is obtained by determining the first extent of a representation of the subject under examination based on the first MR signal. In addition, a relative measure for the outputted gradient moment of the second readout gradient is determined by determining the second extent of a representation of the subject under examination based on the second MR signal. The ratio between the first extent and the second extent describes a ratio between the outputted gradient moments of the first readout gradient and the second readout gradient, where the actually outputted temporal waveforms of the first readout gradient and the second readout gradient may remain undetermined.

It is known from the prior art that a resolution of k-space along the dimension of the readout gradient is determined by the gradient moment output during sampling. Hence, knowing a sampling rate, it is possible to infer the outputted gradient moment from the MR signal.

In a further embodiment, at least one additional gradient along the readout dimension and/or an excitation pulse may be output after the output of the first readout gradient and before the output of the second readout gradient. For example, in the case that the method for determining the correction factor is integrated as part of an image acquisition sequence, the image acquisition sequence may include a plurality of time windows. Each of the plurality of time windows may not be sufficient for the entire proposed method. The output of the first readout gradient including the readout of the first MR signal may be separated in time from the output of the second readout gradient including the readout of the second MR signal (e.g., into two separate time windows within a calibration phase of the image acquisition sequence). The plurality of time windows that are used to perform a method according to the present embodiments may be interrupted by the output of additional gradients along the readout dimension and/or excitation pulses.

In a further embodiment, in order to determine the first extent and/or the second extent of a representation of the subject under examination, a parameterized point spread function is fitted to the associated MR signal in k-space independently in each case. In addition, in this embodiment, the first extent and/or the second extent is determined by at least one parameter of the respectively fitted and parameterized point spread function. In other words, an extent of the representation of the subject under examination in image space may be determined directly based on the MR signal in k-space without producing an MR image. Prior knowledge of the transformation between the MR signal and the MR image, which includes an inverse Fourier transform in at least one dimension, may be used here to determine the extent of the representation on the basis of the MR signal.

If a parameterized point spread function is fitted to the corresponding MR signal, then a resolution of the representation in image space may be obtained by at least one of the parameters. This may be done, for example, by determining zero points in the point distribution function in k-space and/or determining a width of the point distribution function in k-space. Using the known k-space sampling rate, it is possible to determine the extent of the representation from the determined resolution of the representation in image space.

In a further embodiment, a trapezoidal temporal waveform is specified for the first readout gradient or the second readout gradient, where a sinusoidal temporal waveform is specified for the other readout gradient in each case. Whereas a trapezoidal temporal waveform of the readout gradient is particularly easy to implement technically, the sinusoidal temporal waveform allows the readout gradient to be output with particularly low noise. This may, for example, be for reducing stress to the subject under examination during an MR examination.

In a further embodiment, a plurality of first and/or second readout gradients are output successively in time. In this case, immediately consecutive readout gradients may be specified to have an initial polarity that is opposite to the final polarity of the readout gradient that precedes in each case. In addition, a plurality of first and/or second MR signals are read out, one each during each output of the plurality of first and/or second readout gradients. The final polarity denotes, for example, the polarity of the readout gradient that is specified immediately in time before the output of the subsequent readout gradient. The output of the plurality of first and/or second readout gradients allows a portion of k-space to be sampled repeatedly, where the plurality of MR signals are each read out at a different echo time after the output of the at least one excitation pulse. Reversing the polarity of time-successive readout gradients causes, for example, a reversal in the readout direction along the readout dimension in k-space. This embodiment may be configured as an interleaved output of the plurality of first and/or second readout gradients. The sampling along one readout direction may, for example, be performed in each case by the same readout gradient.

Without additionally outputting a phase-encoding gradient, the repeatedly sampled k-space row may be distinguished, for example, based on the respective echo times of the MR signal. The first extent and the second extent of the representation of the subject under examination may each be determined individually by the repeatedly sampled k-space row. In this case, it may be beneficial for the readout gradient (e.g., first or second readout gradient) that was output during the acquisition of the MR signal acquired at the echo time concerned to be assigned to the corresponding sampling of the k-space row.

In a further embodiment, at least one phase-encoding gradient is output before and/or during the output of the first readout gradient and the second readout gradient. The first MR signal and the second MR signal may each be phase-encoded thereby. This allows the MR signal to be resolved in two dimensions in k-space. If the first readout gradient and/or the second readout gradient has a temporal waveform that includes portions of time containing portions of the waveform that are of opposite polarity and equal magnitude, then the readout direction may be reversed portion by portion. If a phase-encoding gradient is output, for example, at the time of every zero crossover of the temporal waveform of the first readout gradient and/or the second readout gradient, then a plurality of frequency-encoded and phase-encoded MR signals may be read out. The plurality of MR signals represent, for example, a plurality of different k-space rows.

If there is no repeated output of an excitation pulse during the readout of the plurality of MR signals, then the different phase-encoded MR signals are read out at a different echo time.

In a further embodiment, in order to determine the first extent and/or the second extent of a representation of the subject under examination, at least one row of pixel values in image space of a first MR image and/or second MR image is produced by the associated MR signal. The first extent and/or the second extent is determined in this case from the at least one row of pixel values in the associated image space. The at least one row of pixel values may be produced based on, for example, the MR signal in k-space by an inverse Fourier transform in at least one dimension. An extent of the representation of the subject under examination in the associated image space of the first MR image and/or the second MR image may be determined, for example, based on intensity levels of the pixel values. In this case, an integration and/or summation of a plurality of intensity levels of the pixel values along the at least one row may be used to determine the first extent and/or the second extent.

If phase encoding is also achieved by the output of a phase-encoding gradient, then it is possible to produce a plurality of rows of pixel values in image space of the associated MR image. The extent of the representation of the subject under examination may thereby be determined (e.g., independently) in the plurality of rows of pixel values. This may achieve greater accuracy.

In a further embodiment, at least one row of pixel values in image space of the first image and second image may be produced for each image by the associated MR signal. In this case, the ratio between the first extent and the second extent may be obtained by transforming a registration between the representation of the subject under examination in the at least one row of pixel values in image space of the first image and the second image. By transforming the registration, it is thus possible to obtain the ratio of the first extent and the second extent directly (e.g., without separately determining the first extent and the second extent). This is advantageous to determining the correction factor from the ratio in a particularly time-efficient and accurate manner.

In a further embodiment, in order to produce the at least one row of pixel values in image space of the first MR image and/or the second MR image, a dataset that includes the associated MR signal of the subject under examination is produced. In this process, each of the MR signals contained in the dataset is padded with an equal number of leading and trailing zeros. The at least one row of pixel values in image space of the first image and/or the second image is produced in the respective image space using the dataset at a higher resolution than the MR signal. Padding with an equal number of leading and trailing zeros may result in interpolation of the respective MR signal when producing the MR image. This may achieve greater accuracy (e.g., in determining the extent of the representation of the subject under examination in image space of the MR image). In addition, it is possible to reduce partial volume effects when producing the MR image. In addition, after the acquisition of a plurality of rows in k-space (e.g., by additional phase-encoding of the MR signal), it is possible to perform particularly suitable zero-padding of k-space (e.g., according to a predefined k-space dimension). The interpolation of the MR signal in producing the MR image may allow the extent of the representation of the subject under examination to be determined in a dimension that, for example, does not correspond to an encoding dimension of the MR examination. This may be advantageous, for example, for anisotropic subjects under examination.

In a further embodiment, the first extent and the second extent of the representation of the subject under examination are determined by a parameter of a parameterized line shape in each case (e.g., a full width at half maximum). The parameterized line shape for obtaining the one parameter in each case is fitted to the at least one row of the first image and of the second image independently for each image. The extent of the representation of the subject under examination may be determined particularly robustly and accurately by the fitting of a parameterized line shape to the at least one row of each image. For example, a parameterized line shape may be predefined at least according to a defined anatomical region of the subject under examination, which is contained in the MR image. When using a parameter of the fitted, parameterized line shape to determine the extent, a full width at half maximum and/or information on zero points of the fitted, parameterized line shape may be advantageous.

In a further embodiment, when determining the first extent and the second extent of the representation of the subject under examination, a first derivative of pixel values is calculated along a predefined direction in the first MR image and the second MR image. The predefined direction includes, for example, at least one directional component along the readout dimension. It may thus be provided that the first extent and the second extent may be used to obtain a reference value for correcting the gradient moment of the second readout gradient that is output along the readout dimension. In addition, determining the first extent and the second extent may include determining minimum and/or maximum points of the first derivative in the first MR image and the second MR image. In other words, calculating the first derivative may make it possible to automatically determine the extent of the representation of the subject under examination along a predefined dimension. For example, computer-aided recognition of the subject under examination may be performed in the at least one row of pixel values by determining the minimum and/or maximum points of the first derivative.

In a further embodiment, the correction factor is determined as part of a sequence (e.g., a segmented echo-planar sequence). The sequence may be partitioned in time into at least a calibration phase and an image acquisition phase. In addition, the correction factor may be determined in the calibration phase, where the correction factor is used to specify at least one additional readout gradient in the image acquisition phase of the sequence. For example, the correction factor may be determined within a calibration phase that is part of an image acquisition sequence (e.g., a necessary part). In other words, determining the correction factor as part of a sequence allows the correction factor to be used directly in the image acquisition phase of the sequence.

In a further embodiment, the image acquisition phase may include the output of a gradient along the readout dimension for prephasing the magnetization, the output of an additional readout gradient along the readout dimension, and the acquisition of an MR representation of the subject under examination. For example, an excitation pulse may be output in order to excite the magnetization out of a state of equilibrium. In addition, a temporal waveform of the gradient along the readout dimension for prephasing the magnetization that corresponds to the temporal waveform of the first readout gradient or the second readout gradient from the calibration phase may be specified. The gradient along the readout dimension for prephasing the magnetization may be specified by an integer multiple of a predefined gradient moment.

In addition, a parameter value may be specified by the correction factor, where the parameter value specifies for each readout gradient of the plurality of additional readout gradients a temporal waveform that corresponds to the temporal waveform of the first readout gradient or the second readout gradient from the calibration phase. It is also possible to, for example, specify for each readout gradient of the plurality of additional readout gradients the temporal waveform that is not specified for the gradient along the readout dimension for prephasing the magnetization.

By adjusting the parameter value, the plurality of additional readout gradients may each be output with an integer multiple of the predefined gradient moment. At least one phase-encoding gradient may be output before and/or during each output of the gradient along the readout dimension for prephasing the magnetization and/or each output of the plurality of additional readout gradients. For example, a phase-encoding gradient (e.g., a phase blip gradient) may be output before each readout gradient of the plurality of additional readout gradients. In addition, a gradient along the phase-encoding dimension for prephasing may be output during the output of the gradient along the readout dimension for prephasing. It is thereby possible to achieve additional prephasing of the magnetization along the phase-encoding dimension.

An MR signal may be read out during each output of the plurality of additional readout gradients. This may make it possible to produce the MR representation of the subject under examination using the plurality of MR signals.

By outputting the gradient along the readout dimension for prephasing the magnetization along the readout dimension at the start of the image acquisition phase, a gradient echo may subsequently be generated during the output of each readout gradient of the plurality of additional readout gradients.

In the sequence, the output of the gradient along the phase-encoding dimension for prephasing may facilitate phase encoding in k-space. In this process, one row in k-space is selected in conjunction with each output of the plurality of additional readout gradients.

For example, when the plurality of additional readout gradients are output in immediate succession in time, it may be necessary to specify the plurality of additional readout gradients to have alternating polarity. This may facilitate reversal of the readout direction along the readout dimension with each reversal in polarity of the additional readout gradients (e.g., at a zero crossover of the temporal waveform). If no additional excitation pulse is output between or during the readout of the plurality of MR signals, then the plurality of MR signals may be read out each at a different echo time.

For example, for a segmented echo-planar sequence, an integer multiple of a predefined gradient moment is often specified for the gradient along the readout dimension for prephasing the magnetization. The predefined gradient moment in this case often describes an extent of a k-space segment along the readout dimension. Segmented sampling of k-space may be facilitated by, for example, specifying an integer multiple of the predefined gradient moment for each readout gradient of the plurality of additional readout gradients.

The advantages lie, for example, in the possibility of acquiring an MR image of a subject under examination particularly efficiently after a single excitation pulse. For example, motion artifacts may be avoided by the highly time-efficient sequence. A representation of rapidly progressing physiological processes that has a high time resolution is possible.

It is also known from the prior art that for accurate calibration of the MR examination, the main magnetic field in a region under examination of the subject under examination is often adjusted by a shimming device. In this case, an embodiment of the method may be integrated in the calibration phase of the sequence without involving any additional measurement time. The correction factor may be used to adjust the parameter value in the image acquisition phase. Compared with the prior art, the method is suitable for time-efficient and automated determination of the correction factor because there is no need to produce a first and second two-dimensional MR image.

In a further embodiment, the image acquisition phase may include outputting a gradient along the readout dimension for rephasing the magnetization, where the gradient along the readout dimension for rephasing the magnetization is specified to have the theoretically identical gradient moment to the gradient along the readout dimension for prephasing the magnetization. In this case, the gradient along the readout dimension for rephasing the magnetization may be specified to have a polarity that is opposite to the gradient along the readout dimension for prephasing the magnetization.

If a gradient has been output along the phase-encoding dimension for prephasing, a gradient may be output along the phase-encoding dimension for rephasing the magnetization. In this case, the gradient along the phase-encoding dimension for rephasing the magnetization is specified to have the theoretically identical gradient moment and opposite polarity to the gradient along the phase-encoding dimension for prephasing.

A position in the center of k-space may be encoded by outputting the gradients along the readout dimension and along the phase-encoding dimension for rephasing the magnetization.

In a further embodiment, the correction factor is determined repeatedly within a sequence. For example, when examining physiological processes over a prolonged time period, the increased measurement duration may cause heating of individual components of the magnetic resonance system. In addition, movement of the subject under examination and/or other changes in the subject under examination may make it necessary to recalibrate parameter values of the sequence. In this case, it may be advantageous to determine the correction factor repeatedly (e.g., regularly and/or irregularly and/or as a result of a trigger and/or depending on additional parameter values). When the correction factor is determined repeatedly, information about the previously determined correction factors and/or additional prior knowledge may be used for improved (e.g., iterative) determination of the correction factor. This may increase the accuracy in determining the correction factor.

If there is a need for repeated calibration of parameter values of the sequence, the repeated determination of the correction factor may be performed as part of this calibration without involving additional time.

In a further embodiment, a plurality of correction factors are determined within a sequence for acquiring a plurality of slices of a subject under examination, where each correction factor of the plurality of correction factors is determined individually for each slice of the plurality of slices. Determining a plurality of correction factors within a sequence (e.g., slice by slice) allows particularly accurate correction of the theoretically identically specified gradient moments of the first readout gradient and the second readout gradient. For example, one correction factor may be determined for each of the acquired slices.

In addition, a magnetic resonance system that is configured to perform an embodiment of the method is provided. The magnetic resonance system includes an RF processing unit, a gradient control unit, a sequence control unit, and a processing unit. The magnetic resonance system is configured to produce a plurality of MR images using the RF processing unit, the gradient control unit, the sequence controller, and the processing unit. For this purpose, the magnetic resonance system may use the gradient control unit to output, for example, a gradient along the readout dimension for prephasing a magnetization. Then, a first readout gradient may be output by the gradient control unit. In addition, the magnetic resonance system is configured to read out at least one first MR signal from the subject under examination during the output of the first readout gradient. For example, prior thereto, an excitation pulse to deflect the magnetization out of a state of equilibrium may be output by the RF processing unit. In addition, the processing unit may be configured to determine a first extent of a representation of the subject under examination based on the one first MR signal.

In addition, the processing unit may be configured to specify a second readout gradient having a theoretically identical gradient moment to the first readout gradient. In this case, a temporal waveform that differs from a temporal waveform of the first readout gradient is specified for the second readout gradient. For example, the respective temporal waveforms of the first readout gradient and the second readout gradient may each be specified by a parameter value of a sequence using the sequence control unit.

The gradient control unit may be used to output the second readout gradient along the readout dimension. Reading out a second MR signal of the subject under examination during the output of the second readout gradient may facilitate determination of a second extent of a representation of the subject under examination based on the at least one second MR signal by the processing unit. Then, the processing unit may be used to obtain the correction factor automatically from a ratio between the first extent and the second extent.

For example, the correction factor may be used to adjust a parameter value automatically. The correction factor may thereby be used to automatically fit an additional readout gradient, as part of an image acquisition sequence, to a predefined gradient moment.

In addition, the magnetic resonance system may include a display unit (e.g., a display and/or monitor and/or an LED indicator) that is configured to show information and/or graphical presentations of information from the magnetic resonance system and/or from further components of the magnetic resonance system.

The advantages of the magnetic resonance system of the present embodiments are essentially the same as the advantages of the method for automatically determining a correction factor for producing magnetic resonance images using a magnetic resonance system of the present embodiments. Features, advantages, or alternative embodiments mentioned in this connection may also be applied to the other claimed subject matter, and vice versa.

In addition, a computer program product that includes a program and may be loaded directly into a memory of a programmable processor is provided. The computer program product includes program means (e.g., libraries and auxiliary functions) in order to perform a method for automatically determining a correction factor for producing magnetic resonance images using a magnetic resonance system, when the computer program product is executed. The computer program product may include software containing a source code that still needs to be compiled and linked or just needs to be interpreted, or an executable software code that, for execution, only needs to be loaded into the processing unit. A method for automatically determining a correction factor for producing magnetic resonance images using a magnetic resonance system may be performed by the computer program product quickly, repeatedly in an identical manner, and robustly. The computer program product is configured such that the computer program product may perform, using the processing unit, the method acts according to the present embodiments. Therefore, the processing unit is to have the necessary specifications such as, for example, a suitable RAM, a suitable graphics card, or a suitable logic unit, in order to be able to perform the respective method steps efficiently.

The computer program product is stored, for example, on a computer-readable medium (e.g., a non-transitory computer-readable storage medium) or on a network or server, from where the computer program product may be loaded into the processor of a processing unit (e.g., a processor). The processor may be connected directly to the processing unit or may form part of the processing unit. In addition, control data of the computer program product may be stored on an electronically readable data storage medium. The control data (e.g., instructions) in the electronically readable data storage medium may be embodied such that the control data performs a method according to the present embodiments when the data storage medium is used in a processing unit. Examples of electronically readable data storage media are a DVD, a magnetic tape, or a USB stick, on which electronically readable control data is stored (e.g., software). When this control data is read from the data storage medium and stored in a processing unit, all the embodiments of the above-described method may be performed. Hence, the present embodiments may also proceed from the computer-readable medium and/or from the electronically readable data storage medium.

BRIEF DESCRIPTION OF THE DRAWINGS

Exemplary embodiments of the invention are described in more detail below and illustrated in the drawings. The same reference signs are used for the same features in different figures, in which.

DETAILED DESCRIPTION

Figure 1:
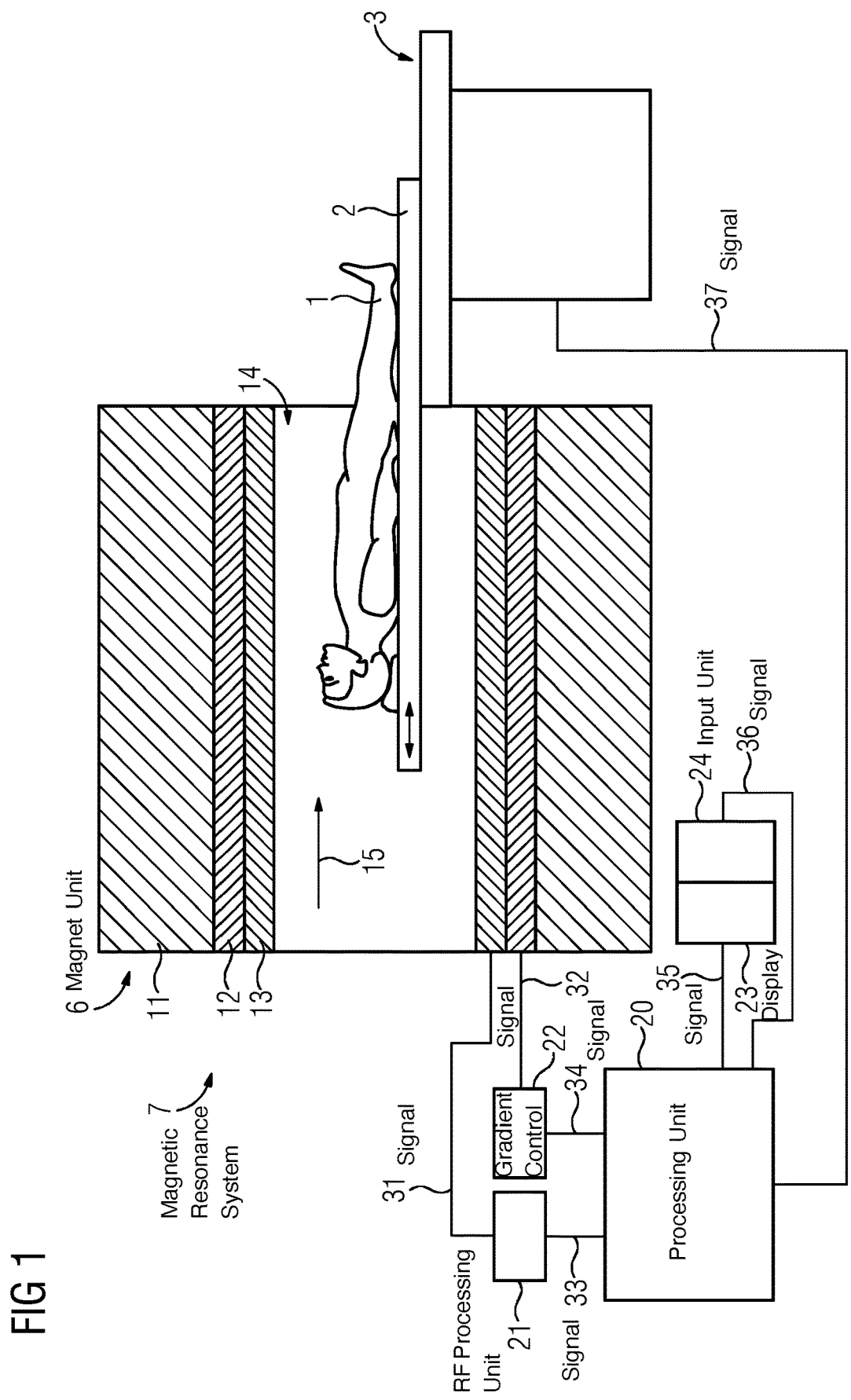
FIG. 1 is a schematic diagram of one embodiment of a magnetic resonance system for performing a method.

FIG. 1 schematically shows a variant of a magnetic resonance system 7 for performing a method of one or more of the present embodiments. The magnetic resonance system 7 includes a magnet unit 6 and a patient placement zone 14. The magnet unit 6 includes, for example, a superconducting main magnet 11 that is configured to generate a strong main magnetic field 15 at a main magnetic field strength that is constant over time. For example, the patient placement zone 14 may have a cylindrical shape, in which the patient placement zone 14 may be enclosed by the magnet unit 6 along an outer surface of the cylinder. The patient placement zone 14 includes, for example, at least one aperture for receiving a patient 1 and a patient support apparatus 2. The patient support apparatus 2 is movably mounted so that the patient 1 may be positioned from a position outside the magnetic resonance system 7 into the patient placement zone 14. A patient table 3 may, for example, support the patient support apparatus 2 and move the patient support apparatus 2, for example, using a motor and/or automatically. A processing unit 20 (e.g. a processor) may send for this purpose a signal 37 to the patient table 3. In an opposite direction, the processing unit 20 may retrieve a current positioning of the patient 1 by retrieving a signal 37 from the patient table 3.

In addition, the magnet unit 6 includes a gradient coil unit 12 configured to generate magnetic field gradients (e.g., readout gradients) for spatial encoding during image acquisition. The gradient coil unit 12 may be controlled by a gradient control unit 22. To do this, the gradient control unit 22 may send a signal 32 to the gradient coil unit 12.

The magnet unit 6 also includes a radio frequency (RF) antenna unit 13 that, in the exemplary embodiment, is in the form of a body coil. The RF antenna unit 13 is permanently integrated in the magnet unit 6 and surrounds the patient placement zone 14. The RF antenna unit 13 is configured to deflect a magnetization. The magnetization appears as a net magnetization, where, in a state of equilibrium, proton spins are aligned in parallel in the main magnetic field 15. For example, the polarization may be excited by the output of excitation pulses and/or refocusing pulses. In addition, the RF antenna unit 13 may be controlled by a signal 31 from an RF processing unit 21 (e.g., an RF processor).

The RF antenna unit 13 is also configured to receive MR signals. In this case, the RF antenna unit may send a corresponding signal 31 to the RF processing unit 21.

The gradient control unit 22, the RF processing unit 21, and the main magnet 11 may be controlled, for example, via a processing unit 20 of the magnetic resonance system 7. The signals 33 and 34, for example, may be used bidirectionally for this purpose.

The processing unit 21 may be configured to translate a sequence (e.g., for producing MR images) into signals for the respective components of the magnetic resonance system 7. This may allow a sequence to be implemented during an MR examination. In addition, the processing unit 21 may be configured to process the MR signals received from the RF antenna unit 13 and, for example, to produce MR images therefrom.

The magnetic resonance system 7 also includes a display unit 23 configured to display parameter values of a sequence and/or MR images. The processing unit 20 may send for this purpose a signal 25 to the display unit 23. The display unit 23 may be in the form of a monitor and/or display. In addition, the magnetic resonance system 7 may include an input unit 24 (e.g., a keyboard and/or a touchscreen and/or a button arrangement) configured to send, via a signal 36, an input by an operator to the processing unit 20.

Control of the patient support apparatus 2 may likewise be facilitated by an input by an operator at the input unit 24. In this process, the processing unit 20 may send a signal 37 to the patient table 3, thereby facilitating automatic and/or semi-automatic positioning of the patient 1 relative to an isocenter of the magnetic resonance system 7.

The magnetic resonance system 7 is configured to implement an embodiment of the method for automatically determining a correction factor for producing magnetic resonance images.

Figure 2:
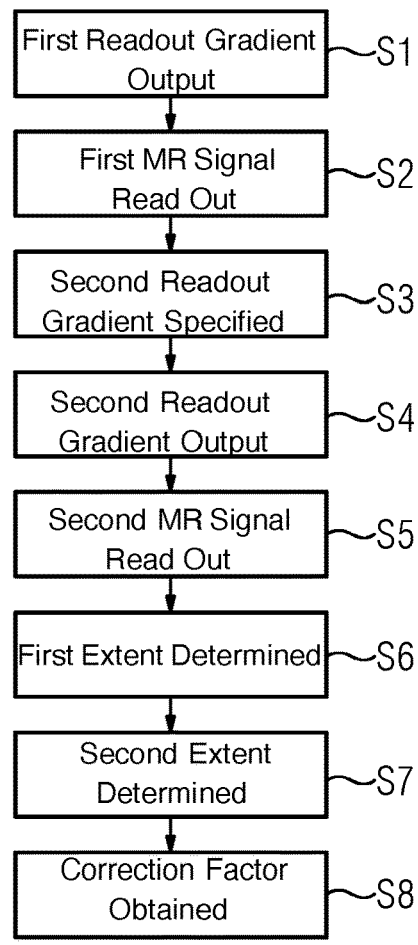
FIG. 2 is a schematic flow diagram of one embodiment of a method for automatically determining a correction factor.

FIG. 2 shows a schematic flow diagram of the method for automatically determining a correction factor. In act S1, a first readout gradient may be output along a readout dimension. In act S2, during the output of the first readout gradient, a first MR signal from the subject under examination may be read out (e.g., acts S1 and S2 at least partially overlap each other in time). In act S3, a second readout gradient may be specified having a theoretically identical gradient moment to the first readout gradient. In this case, a temporal waveform that differs from a temporal waveform of the first readout gradient may be specified for the second readout gradient. In act S4, the second readout gradient may be output along the readout dimension. In act S5, during the output of the second readout gradient, a second MR signal from the subject under examination may be read out (e.g., acts S4 and S5 at least partially overlap each other in time). In addition, in act S6, a first extent of a representation of the subject under examination may be determined based on the first MR signal. In addition, in act S7, a second extent of a representation of the subject under examination may be determined based on the second MR signal. Thereafter, in act S8, a correction factor may be obtained from a ratio between the first extent and the second extent. Act S6 may also be performed parallel in time with one or more of acts S3 to S7. For example, act S6 may also be performed immediately after act S2.

Figure 3:
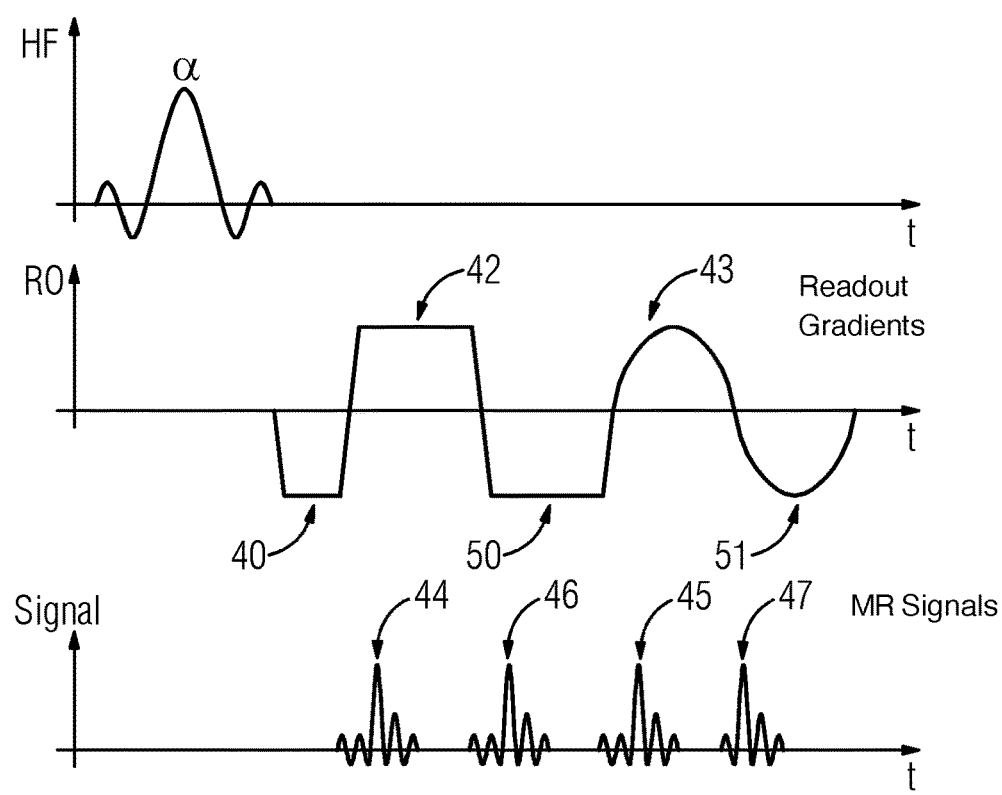
FIG. 3 is a schematic diagram of an exemplary sequence for automatically determining a correction factor.

FIG. 3 shows a schematic diagram of an embodiment of a sequence for automatically determining a correction factor. In this embodiment, an excitation pulse a for deflecting or exciting a magnetization out of a state of equilibrium is output by the RF antenna unit 13. Then, a gradient for prephasing 40 the magnetization may be output along the readout dimension RO with a specified polarity by the gradient coil unit 12.

Thereafter, a plurality of first and/or second readout gradients may be output successively in time. The first readout gradient is specified to have an initial polarity that is opposite to the polarity of the gradient along the readout dimension for prephasing 40. In addition, consecutive readout gradients 42, 50, 42 and 51 may each be specified to have an initial polarity that is opposite to the final polarity of the readout gradient that precedes in each case.

A plurality of first and/or second MR signals 44 to 47 may be read out, one each during each output of the plurality of first and/or second readout gradients. For example, two first MR signals 44 and 46 may be read out during the output of the two first readout gradients 42 and 50, and two second MR signals 45 and 47 may be read out during the output of the two second readout gradients 43 and 51.

FIG. 3 shows an embodiment in which two first readout gradients 42 and 50, and two second readout gradients 43 and 51 are in each case output in immediate succession in time. In this embodiment, immediately consecutive readout gradients are specified to have an alternating polarity. Reversing the polarity of the particular readout gradient causes a reversal in a readout direction along the readout dimension RO (e.g., at each zero crossover of the temporal waveform).

In this embodiment, both the gradient along the readout dimension for prephasing 40 and the two first readout gradients 42 and 50 are each specified to have a trapezoidal temporal waveform. The two second readout gradients 43 and 51 are, for example, specified to have a sinusoidal temporal waveform. This may achieve, for example, low-noise output of the plurality of second readout gradients.

A first extent of a representation of the subject under examination 1 may be determined based on the two first MR signals 44 and 46. In addition, a second extent of a representation of the subject under examination 1 may be determined based on the two second MR signals 45 and 47. The correction factor may be determined from a ratio between the first extent and the second extent.

The plurality of first MR signals and second MR signals may be averaged, for example, in order to determine the first extent and the second extent of the respective representations of the subject under examination 1. This may facilitate greater accuracy in determining the first extent and the second extent.

In this embodiment, a plurality of first readout gradients and a plurality of second readout gradients, for example, are output successively in time. If there is a discrepancy between the theoretically specified identical gradient moment of the plurality of first readout gradients and second readout gradients, the respectively sampled k-space row may be shortened or lengthened depending on the nature of the discrepancy. If an even number of first readout gradients and an even number of second readout gradients are output, any drift along the readout dimension in k-space may be avoided.

Figure 4:
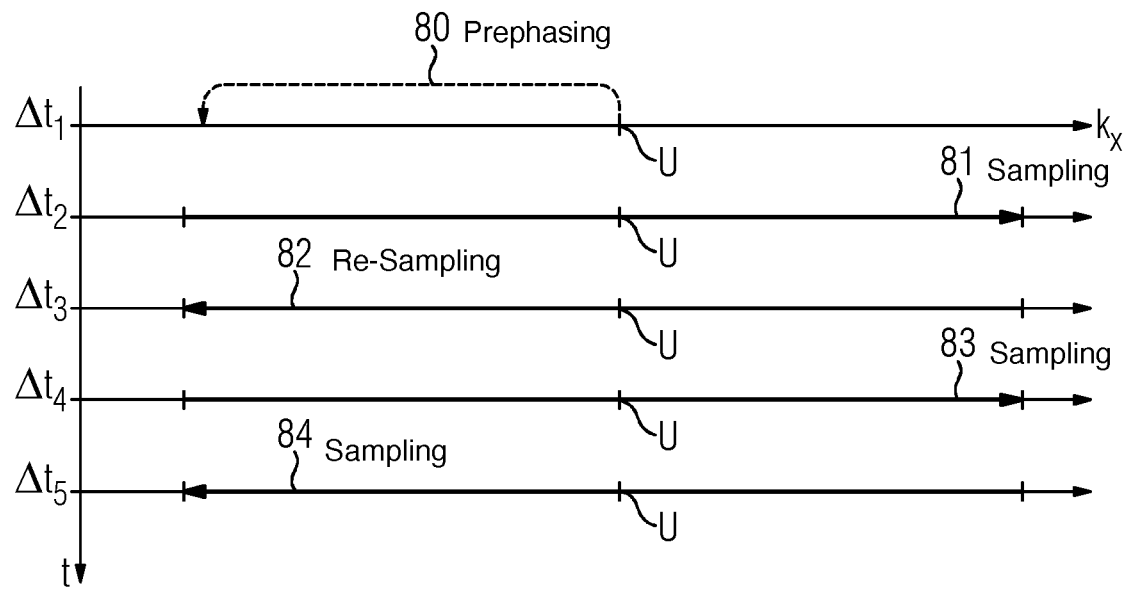
FIG. 4 is a schematic diagram of exemplary one-dimensional k-space sampling for determining a correction factor.

FIG. 4 shows a schematic diagram of one-dimensional k-space sampling for determining a correction factor according to the embodiment shown in FIG. 3. FIG. 3 shows the sampling of a k-space row along a readout dimension in k-space $k_x$ over the course of time along a time axis t. Proceeding from a center U of k-space, by outputting the gradient along the readout dimension for prephasing 40 during the time period $\Delta t_1$, sampling may begin outside the center U of k-space.

The fact that the first readout gradient 42 is specified to have an initial polarity that is opposite to the polarity of the gradient along the readout dimension for prephasing provides that after the prephasing 80, the readout direction along the readout dimension in k-space $k_x$ is reversed.

During the output of the first readout gradient 42 in the time period $\Delta t_2$, first sampling 81 of the k-space row may take place along a readout direction, where the readout direction is determined by the polarity of the first readout gradient 42. The first MR signal 44 may be read out in this process. According to the sequence shown in FIG. 3, an additional first readout gradient 50 may be output, with the initial polarity of the consecutive readout gradients being specified to be opposite the final polarity of the readout gradient that precedes in each case. This achieves a reversal in the readout direction in k-space when the second first readout gradient 50 is output. During the output of the second first readout gradient 50 in the time period $\Delta t_3$, the k-space row is re-sampled 82 in the reverse readout direction. The second first MR signal 46 may be read out in this process.

According to act S5, two second readout gradients 43 and 51 may be output successively in time. In this process, once again, sampling 83 and 84 of the same k-space row takes place in time periods $\Delta t_4$ and $\Delta t_5$, respectively, in the reverse readout direction in each case. Second MR signals 45 and 47 may be read out, one each during the respective samplings 83 and 84.

According to an embodiment of the method, in order to determine the first extent and/or the second extent of a representation of the subject under examination 1, a parameterized point spread function is fitted to the associated MR signal in k-space independently in each case. The first extent and/or the second extent may be determined by at least one parameter of the respectively fitted and parameterized point spread function. Referring to the exemplary embodiment shown in FIGS. 3 and 4, by sampling the same k-space row twice for the temporal waveform of the first readout gradient and twice for the temporal waveform of the second readout gradient, the first extent and the second extent may be determined more accurately. By adjusting a parameterized point spread function in order to determine the first extent and/or the second extent, it is possible, for example, to dispense with producing an MR image.

Figure 5:
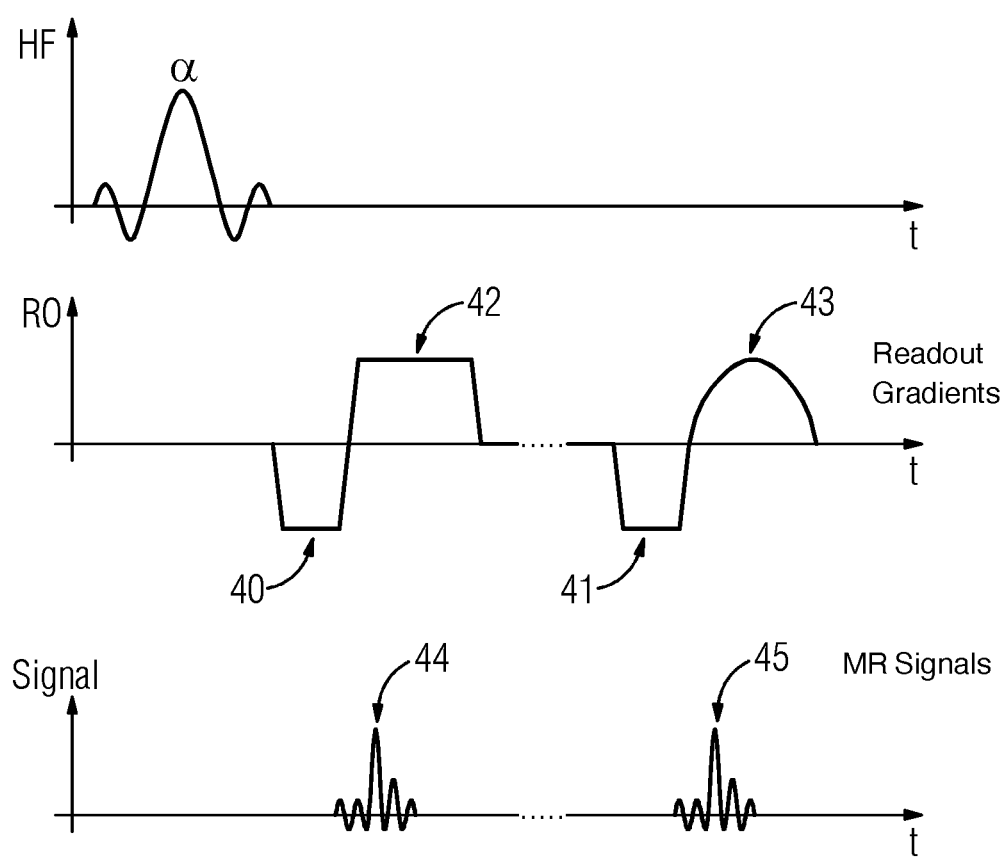
FIG. 5 is a schematic diagram of an exemplary sequence for automatically determining a correction factor including respective gradients along the readout dimension for prephasing.

FIG. 5 shows a schematic diagram of an exemplary sequence for automatically determining a correction factor including respective gradients along the readout dimension for prephasing 40 and 41. According to an embodiment of the method, after the output of one or more first readout gradients 42 successively in time, and before the output of the at least one second readout gradient 43, an additional gradient may be output along the readout dimension for prephasing 41 the magnetization. For example, in the case that an additional gradient along the readout dimension and/or an excitation pulse is output after the output of the first readout gradient 42 and before the output of the second readout gradient 43, the first MR signal 44 and the second MR signal 45 may be read out separately in time. The output of the additional gradient along the readout dimension and/or the excitation pulse before the output of the second readout gradient 43 includes a gradient and/or excitation pulse for rephasing the magnetization along the readout dimension.

The additional gradient along the readout dimension for prephasing 41 may be specified to have an initial polarity that is opposite to the final polarity of the first readout gradient 42. In addition, the second readout gradient 43 may be specified to, for example, have an initial polarity that is opposite to the polarity of the additional gradient along the readout dimension for prephasing 41.

The output of the additional gradient along the readout dimension for prephasing 41 may allow sampling of the same k-space row during the output of the second readout gradient 43 as for the output of the first readout gradient 42.

Figure 6:
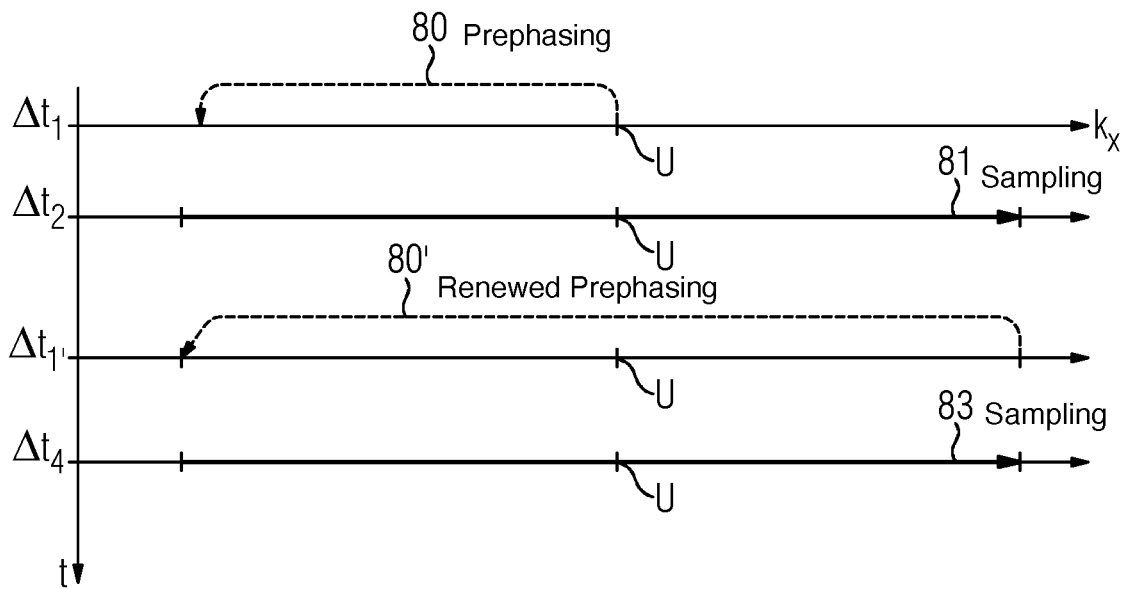
FIG. 6 is a schematic diagram of an exemplary one-dimensional k-space sampling for determining a correction factor using interposed prephasing.

FIG. 6 shows a schematic diagram of the one-dimensional k-space sampling according to a sequence such as proposed in FIG. 5. First, prephasing 80 of the magnetization out of the center U of k-space is achieved in the first time period $\Delta t_1$ by outputting the gradient along the readout dimension for prephasing 40. In addition, first sampling 81 of the k-space row during the time period $\Delta t_2$ may take place during the output of the first readout gradient 42. Thereafter, the output of the additional gradient along the readout dimension for prephasing 41 may facilitate renewed prephasing 80' of the magnetization during the time period $\Delta t_1'$. Then, the k-space row (e.g., the same k-space row) may be sampled 83 during the output of the second readout gradient 43 in the time period $\Delta t_4$.

Figure 7:
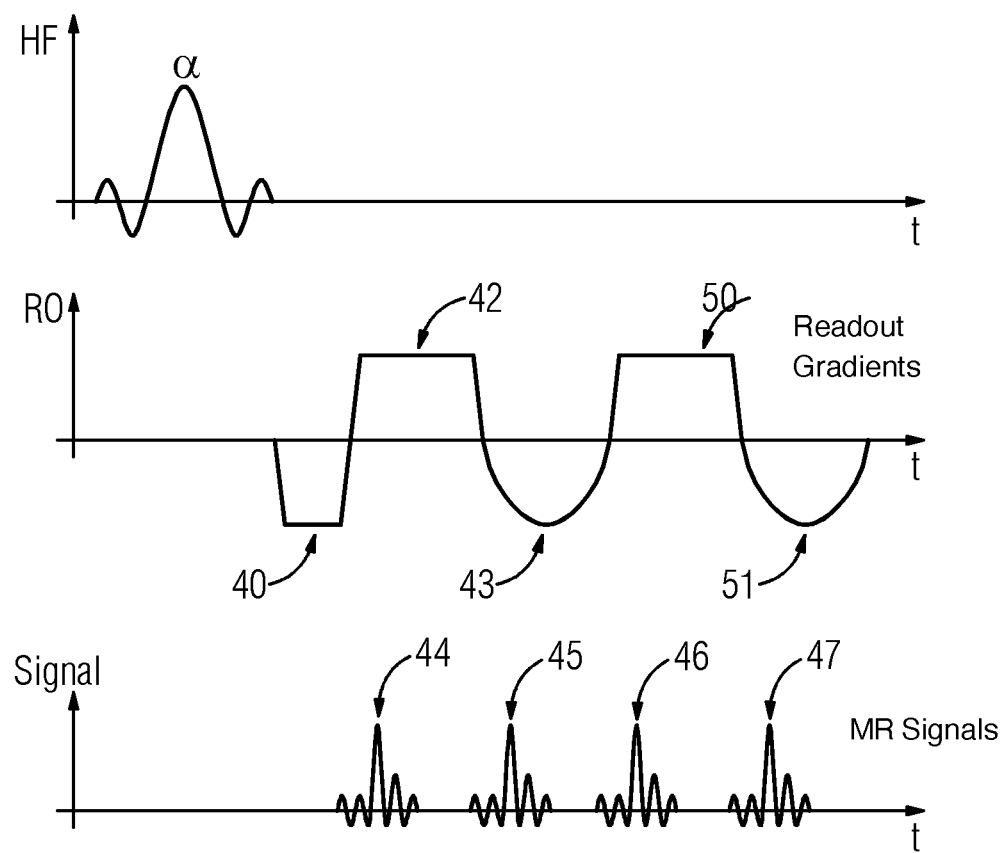
FIG. 7 is a schematic diagram of an exemplary sequence for automatically determining a correction factor, where first and second readout gradients are output in an interleaved manner.

FIG. 7 shows a schematic diagram of a sequence for automatically determining the correction factor, where the first readout gradient and the second readout gradient are output in an interleaved manner. This embodiment is similar to the embodiment shown in FIG. 3 in that a plurality of first and second readout gradients are output successively in time. The interleaved output of first and second readout gradients, however, allows a readout direction that is constant over time for the first readout gradients and, respectively, for the second readout gradients. In other words, a readout direction is specified for the first readout gradients, where the second readout gradients are specified in the reverse readout direction. This is achieved, for example, by an alternating polarity of the first and second readout gradients, which are interleaved consecutively in time. In terms of the k-space sampling, the sequence again results in repeated sampling of the same k-space row along the readout dimension in k-space $k_x$. The interleaved output of the first and second readout gradients provides that each k-space row is sampled only in one readout direction by the output of the plurality of first readout gradients, and in the reverse readout direction thereto by the output of the plurality of second readout gradients.

This embodiment is beneficial, for example, for high consistency within the first MR signals 44 and 46 and the second MR signals 45 and 47. This may facilitate greater accuracy in determining the first extent and the second extent.

Figure 8:
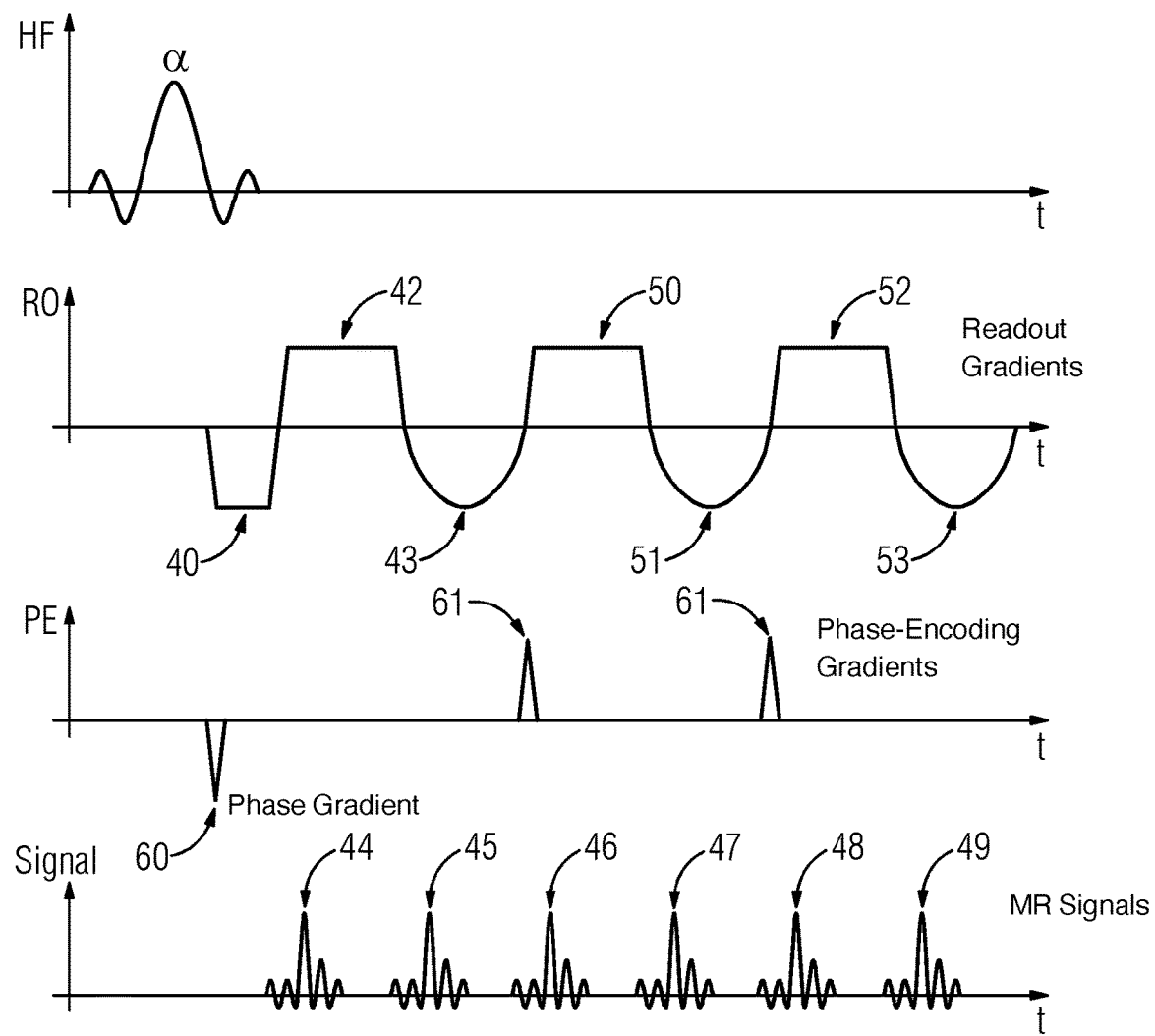
FIG. 8 is a schematic diagram of an exemplary sequence for automatically determining a correction factor using two-dimensional k-space sampling.

FIG. 8 shows a schematic diagram of an exemplary sequence for automatically determining the correction factor using two-dimensional k-space sampling. In this case, a phase gradient for prephasing 60 along a phase-encoding dimension PE is output, for example, simultaneously with the output of the gradient for prephasing 40 along the readout dimension RO. It is thereby possible to achieve prephasing of the magnetization along the readout dimension RO and the phase-encoding dimension PE. Then, a plurality of first and second readout gradients may be output successively in time in an interleaved manner. During the output of the first readout gradient 42, a k-space row is sampled along a readout direction according to the polarity of the first readout gradient 42. Thereafter, the same k-space row is re-sampled in the reverse readout direction during the output of the first second readout gradient 43.

If at least one phase-encoding gradient is output before and/or during each output of the first readout gradient and/or second readout gradient, then at least one additional k-space row may be sampled. In the embodiment, one phase-encoding gradient 61 along the phase-encoding dimension PE is output after each output of each second readout gradient 43, 51 and 53, or respectively before each output of the subsequent first readout gradients 50 and 52. This may achieve that each of the phase-encoded k-space rows is sampled once by a first readout gradient and once by a second readout gradient. The advantage of the embodiment shown in FIG. 7 of a consistent readout direction for every first readout gradient or every second readout gradient is retained. The plurality of first MR signals 44, 46 and 48 each correspond to, for example, a k-space row that has been sampled during the output of a corresponding first readout gradient. In other words, the output of the plurality of phase-encoding gradients 61 before and/or during each output of the first readout gradient and/or second readout gradient may facilitate two-dimensional sampling of k-space.

The plurality of second MR signals 45, 47 and 49 again correspond to the same k-space rows. The k-space rows are sampled in the reverse readout direction during the output of respective second readout gradients. The first and second extents may, for example, each be determined independently for each of the phase-encoded k-space rows.

In order to determine the first and/or second extent of a representation of the subject under examination 1, at least one row of pixel values in image space of a first and/or second MR image may be produced by the associated MR signal. The first and/or second extent may be determined in this case from the at least one row of pixel values in the associated image space.

In addition, at least one row of pixel values in image space of the first image and second image in each case may be produced by the associated MR signal. In this case, the ratio between the first extent and the second extent may be obtained by transforming a registration between the representation of the subject under examination 1 in the at least one row of pixel values in image space of the first image and of the second image.

Referring to the embodiment shown in FIG. 8, one row of pixel values in image space of a first image and of a second image may be produced for each of the plurality of first and second MR signals 44 to 49.

If at least one row of pixel values in image space of the first image and of the second image is produced by the associated MR signal, the first extent and the second extent may be determined by a parameter of a parameterized line shape in each case. The parameterized line shape for obtaining the one parameter in each case may be fitted to the at least one row of the first image and of the second image independently for each image.

In addition, the first and second extent may also be determined by calculating a first derivative of pixel values along a predefined direction in the first and second MR images. For two-dimensional sampling of k-space, as is the case in the exemplary embodiment, the direction for calculating the first derivative may also be specified to be different from a readout direction. In this case, however, the specified direction includes at least one directional component along the readout dimension of the second readout gradient. Determining the first and second extents includes, in addition, determining minimum and/or maximum points of the first derivative in the first and second MR images. For example, sharp edges of the representation of the subject under examination 1 along the predefined direction are determined by the minimum and/or maximum points of the first derivative.

Zero-padding may be beneficial for greater accuracy in determining the first and second extent from the at least one row of pixel values in the associated image space. In this case, in order to produce the at least one row of pixel values in image space of the first and/or second MR image, a dataset that includes the associated MR signal of the subject under examination 1 may be produced. By padding each of the MR signals contained in the dataset with an equal number of leading and trailing zeros, the at least one row of pixel values in image space of the first and/or second MR image may be produced in the respective image spaces using the dataset at a higher resolution than the MR signal. Depending on the way in which the first and second extents are determined, padding with an equal number of leading and trailing zeros may be performed only for individual MR signals contained in the dataset.

In addition, for two-dimensional sampling of k-space, as proposed in FIG. 8, two-dimensional padding of the plurality of first and/or second MR signals may be performed along the readout dimension RO and along the phase-encoding dimension PE with an equal number of leading and trailing zeros in each case.

Figure 9:
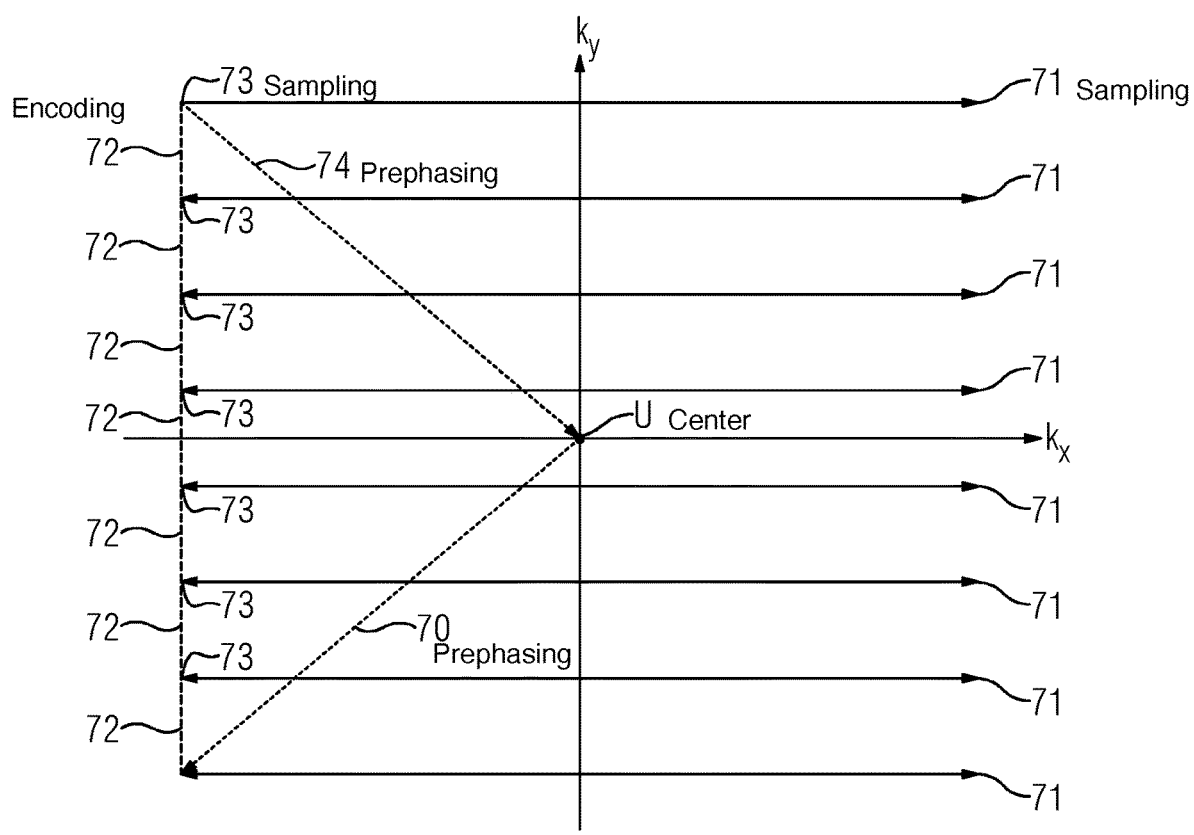
FIG. 9 is a schematic diagram of an exemplary two-dimensional k-space sampling for determining a correction factor with a phase-encoding gradient being output after every two consecutive readout gradients.

FIG. 9 shows a schematic diagram of an exemplary two-dimensional k-space sampling according to the sequence proposed in FIG. 8. In this case, first prephasing 70 of the magnetization takes place along the readout dimension in k-space $k_x$ and along the phase-encoding dimension in k-space $k_y$ during the output of the gradient along the readout dimension for prephasing 40 and of the gradient along the phase-encoding dimension for prephasing 60. Then, sampling 71 of each phase-encoded k-space row takes place during the output of a first readout gradient, and sampling 73 of the same k-space row in the reverse direction takes place during the output of a second readout gradient. A phase-encoding gradient 61 for encoding 72 an additional k-space row is output after each output of a second readout gradient.

Figure 10:
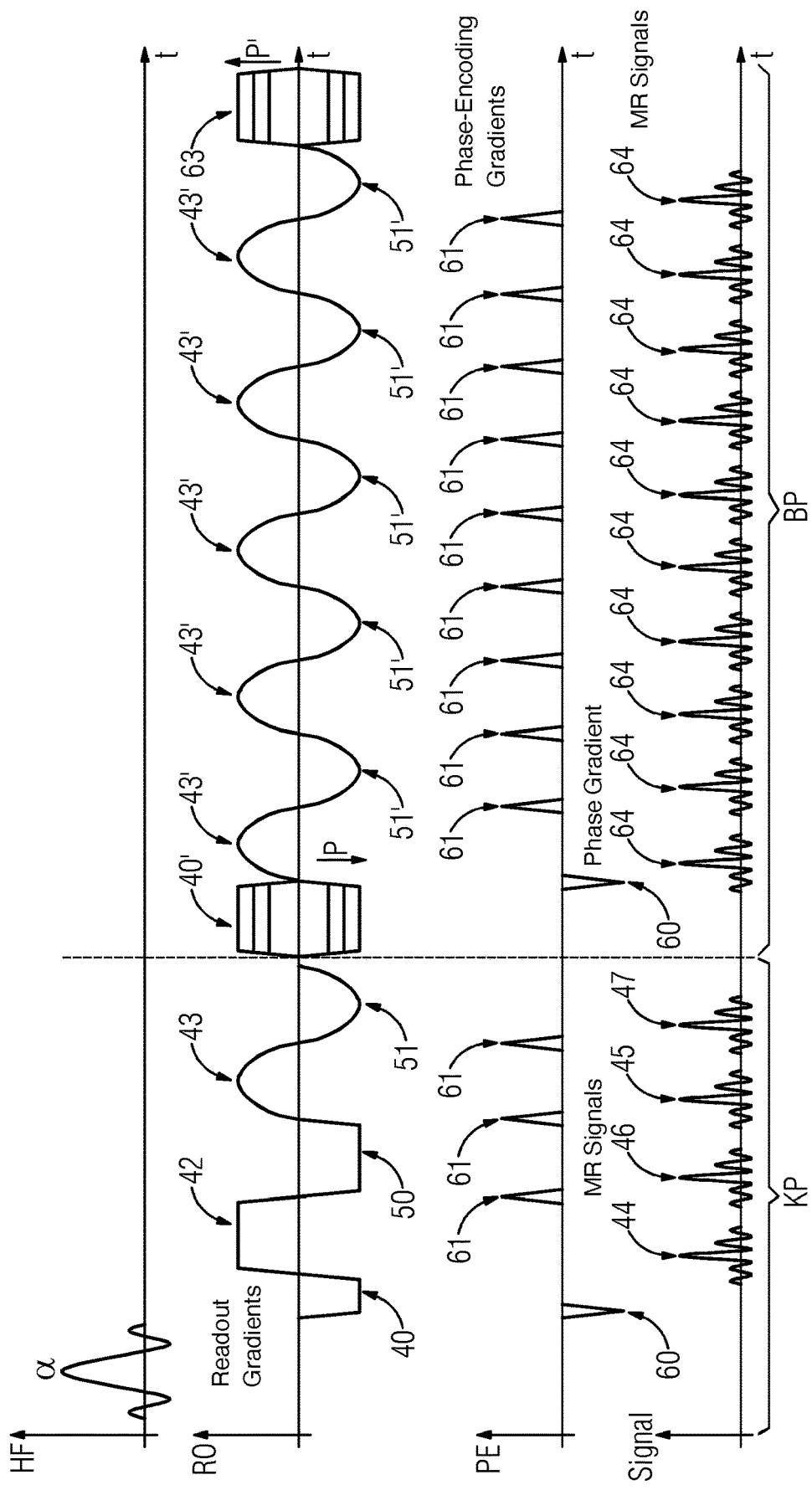
FIG. 10 is a schematic diagram of an exemplary sequence for automatically determining a correction factor and for producing magnetic resonance images.
Figure 11:
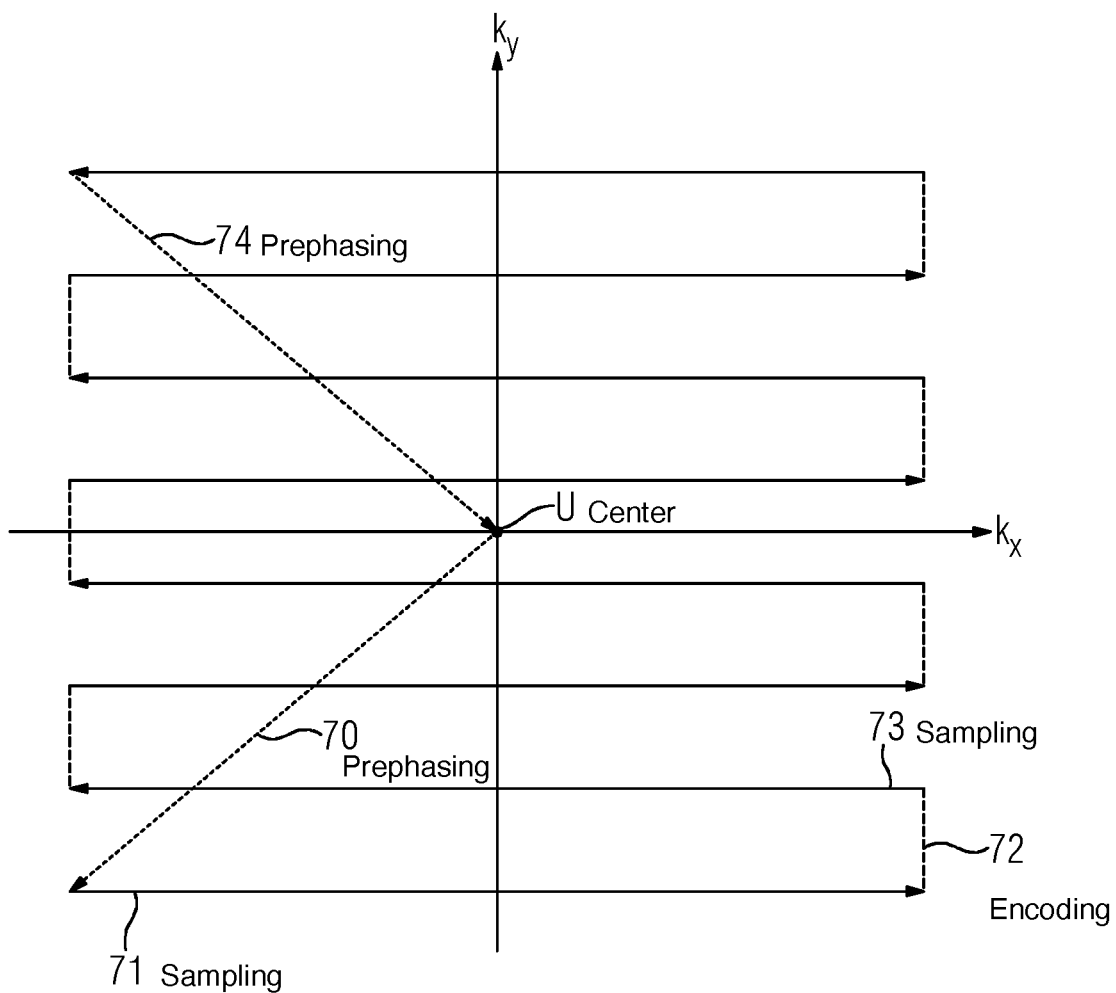
FIG. 11 is a schematic diagram of an exemplary two-dimensional k-space sampling for determining a correction factor.

FIG. 10 shows a schematic diagram of an exemplary sequence for automatically determining a correction factor and for producing magnetic resonance images. The correction factor is determined as part of a sequence. The sequence is partitioned in time into at least a calibration phase KP and an image acquisition phase BP. In addition, the correction factor is determined in the calibration phase KP and is used to specify at least one additional readout gradient 43' in the image acquisition phase BP of the sequence.

FIG. 10 shows an exemplary embodiment of the method that includes the image acquisition phase BP, the output of a gradient along the readout dimension RO for prephasing the magnetization 40', the output of a plurality of additional readout gradients 43' along the readout dimension RO, and the acquisition of an MR representation of the subject under examination 1. A temporal waveform of the gradient along the readout dimension RO for prephasing the magnetization 40' that corresponds to the temporal waveform of the first readout gradient 42 or the second readout gradient 43 from the calibration phase KP may be specified. This gradient along the readout dimension RO for prephasing the magnetization 40' may be specified by an integer multiple of a predefined gradient moment. In addition, a parameter value that, for example, has been determined as part of the calibration phase KP may be specified by the correction factor. The parameter value may specify for each readout gradient of the plurality of additional readout gradients a temporal waveform that corresponds to the temporal waveform of the first readout gradient 42 or of the second readout gradient 43 from the calibration phase KP, which is not specified for the gradient along the readout dimension RO for prephasing the magnetization 40'.

By adjusting the parameter value, the plurality of additional readout gradients 43' may each be output at an integer multiple of the predefined gradient moment. At least one phase-encoding gradient 61 may be output before and/or during each output of the gradient along the readout dimension RO for prephasing the magnetization 40' and/or each output of the plurality of additional readout gradients 43'. For example, a gradient along the phase-encoding direction PE for prephasing the magnetization 60 may be output during the output of the gradient along the readout dimension RO for prephasing the magnetization 40'. An MR signal 64 may be read out during each output of the plurality of additional readout gradients 43'. The MR representation of the subject under examination may thereby be produced by the plurality of MR signals 64.

In addition, the image acquisition phase BP may include the output of a gradient along the readout dimension RO for rephasing the magnetization 63. In this case, the gradient along the readout dimension RO for rephasing the magnetization 63 may be specified to have the theoretically identical gradient moment to the gradient along the readout dimension RO for prephasing the magnetization 40'. The gradient along the readout dimension RO for rephasing the magnetization 63 is specified to have, for example, a polarity P' that is opposite to the polarity P of the gradient along the readout dimension RO for prephasing the magnetization 40.

In addition, the correction factor may be determined repeatedly within a sequence. For this purpose, the sequence may include, for example, a plurality of calibration phases KP, where the plurality of correction factors determined therein may be used in the associated subsequent image acquisition phase BP either individually and/or in a combined form (e.g., as an average).

For example, when acquiring a plurality of slices, a plurality of correction factors may be determined within a sequence for acquiring a plurality of slices of a subject under examination 1. In this case, each correction factor of the plurality of correction factors may be determined for each of the plurality of slices. According to the exemplary embodiment shown in FIG. 10, it may be beneficial to have a dedicated calibration phase KP as part of the sequence (e.g., before acquiring each slice). In addition, when calibrating the sequence over the entire (e.g., multi-slice) acquisition volume of the subject under examination 1, it may be advantageous to determine a plurality of correction factors (e.g., slice-specific correction factors) as part of a preceding calibration phase KP of the sequence.

The schematic diagrams contained in the described figures are not shown to scale and do not depict relative sizes.

The method described in detail above and the presented devices are merely exemplary embodiments that may be modified by a person skilled in the art in many ways without departing from the scope of the invention. In addition, the use of the indefinite article "a" or "an" does not rule out the possibility of there also being more than one of the features concerned. Likewise, the term "unit" does not exclude the possibility that the components in question consist of a plurality of interacting sub-components that may also be spatially distributed if applicable.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for automatically determining a correction factor for producing magnetic resonance (MR) images, the method comprising:
    outputting a first readout gradient along a readout dimension;
    reading out a first MR signal from a subject under examination during the outputting of the first readout gradient;
    specifying a second readout gradient, the second readout gradient having a theoretically identical gradient moment to the first readout gradient;
    specifying a temporal waveform for the second readout gradient that differs from a temporal waveform of the first readout gradient;
    outputting the second readout gradient along the readout dimension;
    reading out a second MR signal from the subject under examination during the outputting of the second readout gradient;
    determining a first extent of a representation of the subject under examination based on the first MR signal;
    determining a second extent of a representation of the subject under examination based on the second MR signal; and
    obtaining the correction factor from a ratio between the first extent and the second extent.

2. The method of claim 1, further comprising outputting at least one additional gradient along the readout dimension, an excitation pulse, or the at least one additional gradient along the readout dimension and the excitation pulse after the outputting of the first readout gradient and before the outputting of the second readout gradient.

3. The method of claim 1, wherein determining the first extent of the representation of the subject under examination, the second extent of the representation of the subject under examination, or the first extent of the representation of the subject under examination and the second extent of the representation of the subject under examination comprises fitting a parameterized point spread function to the associated MR signal in k-space independently in each case,
wherein the first extent, the second extent, or the first extent and the second extent are determined by at least one parameter of the respectively fitted and parameterized point spread function.

4. The method of claim 2, wherein a trapezoidal temporal waveform is specified for the first readout gradient or the second readout gradient, and
wherein a sinusoidal temporal waveform is specified for each gradient of the at least one additional gradient.

5. The method of claim 1, further comprising:
outputting a plurality of first readout gradients, a plurality of second readout gradients, or a plurality of first and second readout gradients successively in time, the plurality of first readout gradients comprising the first readout gradient and the plurality of second readout gradients comprising the second readout gradient; and
reading out a plurality of first MR signals, a plurality of second MR signals, or a plurality of first MR signals and second MR signals, one each during each outputting of the plurality of first readout gradients, the plurality of second readout gradients, or the plurality of first and second readout gradients, the plurality of first MR signals comprising the first MR signal and the plurality of second MR signals comprising the second MR signal.

6. The method of claim 1, further comprising outputting at least one phase-encoding gradient before, during, or before and during the outputting of the first readout gradient, the outputting of the second readout gradient, or the outputting of the first readout gradient and the outputting of the second readout gradient.

7. The method of claim 1, wherein determining the first extent of the representation of the subject under examination, the second extent of the representation of the subject under examination, or the first extent and the second extent of the representation of the subject under examination comprises producing at least one row of pixel values in image space of a first MR image, a second MR image, or the first MR image and the second MR image using the associated MR signal,
wherein the first extent, the second extent, or the first extent and the second extent are determined from the at least one row of pixel values in the associated image space.

8. The method of claim 7, wherein the at least one row of pixel values in image space of the first MR image and the second MR image, respectively, is produced by the associated MR signal, and
wherein the method further comprises obtaining a ratio between the first extent and the second extent, the obtaining of the ratio between the first extent and the second extent comprising transforming a registration between the representation of the subject under examination in the at least one row of pixel values in image space of the first MR image and of the second MR image.

9. The method of claim 7, wherein producing the at least one row of pixel values in image space of the first MR image, the second MR image, or the first MR image and the second MR image comprises producing a dataset, the dataset comprising the associated MR signal of the subject under examination,
wherein each of the MR signals contained in the dataset is padded with an equal number of leading zeros and trailing zeros, and
wherein the at least one row of pixel values in image space of the first MR image, the second MR image, or the first MR image and the second MR image is produced using the dataset.

10. The method of claim 7, wherein the first extent and the second extent of the representation of the subject under examination are determined by a parameter of a parameterized line shape in each case, and
wherein the parameterized line shape for obtaining the one parameter in each case is fitted to the at least one row of the first MR image and of the second MR image independently for each image of the first MR image and the second MR image.

11. The method of claim 10, wherein the parameter of the parameterized line shape is a full width at half maximum.

12. The method of claim 7, wherein determining the first extent and the second extent of the representation of the subject under examination comprises calculating a first derivative of pixel values along a predefined direction in the first MR image and the second MR image,
wherein the predefined direction comprises at least one directional component along the readout dimension, and
wherein determining the first extent and the second extent comprises determining minimum, maximum, or minimum and maximum points of the first derivative in the first MR image and the second MR image.

13. The method of claim 1, wherein the correction factor is determined as part of a sequence,
wherein the sequence is partitioned in time into at least a calibration phase and an image acquisition phase,
wherein the correction factor is determined in the calibration phase, and
wherein the correction factor is used to specify at least one additional readout gradient in the image acquisition phase of the sequence.

14. The method of claim 13, wherein the sequence is a segmented echo-planar sequence.

15. The method of claim 13, wherein the image acquisition phase comprises an output of a gradient along the readout dimension for prephasing magnetization, an output of a plurality of additional readout gradients along the readout dimension, and an acquisition of an MR representation of the subject under examination,
wherein a temporal waveform of the gradient along the readout dimension for prephasing the magnetization that corresponds to the temporal waveform of the first readout gradient or the second readout gradient is specified from the calibration phase,
wherein the gradient along the readout dimension for prephasing the magnetization is specified by an integer multiple of a predefined gradient moment,
wherein a parameter value is specified by the correction factor, wherein the parameter value specifies for each additional readout gradient of the plurality of additional readout gradients a temporal waveform that corresponds to the temporal waveform of the first readout gradient or the second readout gradient from the calibration phase, which is not specified for the gradient along the readout dimension for prephasing the magnetization, wherein by adjusting the parameter value, the plurality of additional readout gradients are each output with an integer multiple of the predefined gradient moment, wherein at least one phase-encoding gradient is output before, during, or before and during each output of the gradient along the readout dimension for prephasing the magnetization, each output of the plurality of additional readout gradients, or each output of the gradient along the readout dimension for prephasing the magnetization and each output of the plurality of additional readout gradients, wherein an MR signal is read out during each output of the plurality of additional readout gradients, and wherein the MR representation of the subject under examination is produced using the plurality of MR signals.

16. The method of claim 15, wherein the image acquisition phase comprises outputting a gradient along the readout dimension for rephasing the magnetization, wherein the gradient along the readout dimension for rephasing the magnetization is specified to have a theoretically identical gradient moment to the gradient along the readout dimension for prephasing the magnetization, and wherein the gradient along the readout dimension for rephasing the magnetization is specified to have a polarity that is opposite to the gradient along the readout dimension for prephasing the magnetization.

17. The method of claim 1, wherein the correction factor is determined repeatedly within a sequence.

18. The method of claim 1, wherein a plurality of correction factors are determined within a sequence for acquiring a plurality of slices of the subject under examination, the plurality of correction factors comprising the correction factor, and wherein each correction factor of the plurality of correction factors is determined for a respective slice of the plurality of slices.

19. A magnetic resonance (MR) system configured to automatically determine a correction factor for producing MR images, the MR system comprising:
a radio frequency (RF) processor;
a gradient controller;
a sequence controller; and
a processor,
wherein the magnetic resonance system is configured to:
produce a plurality of MR images using the RF processor, the gradient controller, the sequence controller and the processor, and wherein the automatic determination of the correction factor comprises:
output of a first readout gradient along a readout dimension;
read out of a first MR signal from a subject under examination during the output of the first readout gradient;
specification of a second readout gradient, the second readout gradient having a theoretically identical gradient moment to the first readout gradient;
specification of a temporal waveform for the second readout gradient that differs from a temporal waveform of the first readout gradient;
output of the second readout gradient along the readout dimension;
read out a second MR signal from the subject under examination during the outputting of the second readout gradient;
determination of a first extent of a representation of the subject under examination based on the first MR signal;
determination of a second extent of a representation of the subject under examination based on the second MR signal; and
obtainment of a correction factor from a ratio between the first extent and the second extent.

20. In a non-transitory computer-readable storage medium that stores instructions executable by one or more processors to automatically determine a correction factor for producing magnetic resonance (MR) images, the instructions comprising:
outputting a first readout gradient along a readout dimension;
reading out a first MR signal from a subject under examination during the outputting of the first readout gradient;
specifying a second readout gradient, the second readout gradient having a theoretically identical gradient moment to the first readout gradient;
specifying a temporal waveform for the second readout gradient that differs from a temporal waveform of the first readout gradient;
outputting the second readout gradient along the readout dimension;
reading out a second MR signal from the subject under examination during the outputting of the second readout gradient;
determining a first extent of a representation of the subject under examination based on the first MR signal;
determining a second extent of a representation of the subject under examination based on the second MR signal; and
obtaining a correction factor from a ratio between the first extent and the second extent.

* * * * *